United States Patent
Cavaleri

(10) Patent No.: US 10,945,970 B2
(45) Date of Patent: Mar. 16, 2021

(54) CURCUMIN-BASED COMPOSITIONS AND METHODS OF USE THEREOF

(71) Applicant: Franco Cavaleri, Surrey (CA)

(72) Inventor: Franco Cavaleri, Surrey (CA)

(*) Notice: Subject to any disclaimer, the term of this patent is extended or adjusted under 35 U.S.C. 154(b) by 207 days.

(21) Appl. No.: 16/111,502

(22) Filed: Aug. 24, 2018

(65) Prior Publication Data

US 2018/0360774 A1  Dec. 20, 2018

Related U.S. Application Data

(63) Continuation-in-part of application No. PCT/CA2018/050275, filed on Mar. 8, 2018.

(60) Provisional application No. 62/469,554, filed on Mar. 10, 2017.

(51) Int. Cl.
| | |
|---|---|
| *A61K 36/00* | (2006.01) |
| *A61K 31/12* | (2006.01) |
| *A61K 9/48* | (2006.01) |
| *A61P 3/06* | (2006.01) |
| *A61K 36/9066* | (2006.01) |

(52) U.S. Cl.
CPC .............. *A61K 31/12* (2013.01); *A61K 9/485* (2013.01); *A61K 9/4858* (2013.01); *A61K 9/4866* (2013.01); *A61P 3/06* (2018.01); *A61K 36/9066* (2013.01); *A61K 2300/00* (2013.01)

(58) Field of Classification Search
None
See application file for complete search history.

(56) References Cited

U.S. PATENT DOCUMENTS

| | | | | |
|---|---|---|---|---|
| 2008/0193573 | A1* | 8/2008 | Gow | A61P 25/28 424/756 |
| 2015/0366815 | A1* | 12/2015 | Teles | A61K 9/485 514/769 |

* cited by examiner

*Primary Examiner* — Qiuwen Mi

(57) ABSTRACT

Methods and compositions for increasing LDL receptor levels in a plurality of cells are disclosed. For example, the methods include providing to the cells a curcumin composition that is at least 15% curcumin II or at least 5% curcumin III, in order to increase LDL receptor levels. In addition, compositions for increasing LDL receptor levels in a plurality of cells are disclosed, which include a curcumin composition consisting of at least 15% curcumin II or at least 5% curcumin III (or combinations of such curcuminoids), along with a pharmaceutically-acceptable solvent, filler, or carrier. Still further, methods and compositions for decreasing MSK1 levels in a plurality of cells are disclosed, which involve administering a curcumin III-enriched composition to the cells.

7 Claims, 12 Drawing Sheets

CURCUMIN-BASED COMPOSITIONS AND METHODS OF USE THEREOF

CROSS-REFERENCE TO RELATED APPLICATIONS

This application is a continuation-in-part application of PCT application serial number PCT/CA2018/050275, filed on Mar. 8, 2018, which claims priority to, and incorporates by reference, U.S. provisional patent application 62/469,554, filed on Mar. 10, 2017.

FIELD OF THE INVENTION

The field of the present invention relates to certain curcumin-containing compositions and methods of use thereof, which can be used to increase low-density lipoprotein cholesterol (LDL) receptor expression levels and thereby lower LDL levels in a plurality of cells or subject. In addition, the field of the present invention relates to certain curcumin-containing compositions and methods of use thereof, which can be used to modulate MSK1 production and thereby ameliorate a variety of health conditions.

BACKGROUND OF THE INVENTION

The health benefits of curcumin, particularly whole turmeric extract, are known and have been demonstrated by researchers in recent years. However, several challenges continue to exist, with respect to the formulation of curcumin-based pharmaceuticals and dietary supplements. More specifically, the most common source of curcumin, the Indian spice turmeric (a member of Zingiberaceae), does not contain a sufficient amount of curcumin to provide an efficacious dose to a subject. In fact, the therapeutic benefits provided by natural curcumin extracts have been relatively modest, very inconsistent, and not well understood. Accordingly, there is a continuing need for improved curcumin-based formulations, which address these current challenges.

The present invention, as described further below, addresses many of the foregoing challenges.

SUMMARY OF THE INVENTION

According to certain aspects of the present invention, methods for increasing low-density lipoprotein cholesterol (LDL) receptor expression levels in a plurality of cells are disclosed (and, by extension, methods of reducing LDL levels in the cells). In certain embodiments, the methods comprise providing to the cells a composition that includes an effective and enriched amounts of curcumin II, curcumin III, or a combination of curcumin II and curcumin III. In certain embodiments, the composition is at least 15% (w/v) curcumin II or, preferably, at least 30% (w/v) curcumin II or, more preferably, at least 50% (w/v) curcumin II or, even more preferably, at least 70% (w/v) curcumin II, such as at least 90% (w/v) curcumin II. In other embodiments, the composition is at least 5% (w/v) curcumin III or, preferably, at least 30% (w/v) curcumin III or, more preferably, at least 50% (w/v) curcumin III or, even more preferably, at least 70% (w/v) curcumin III, such as at least 90% (w/v) curcumin III. In still further embodiments, the composition includes a combination of the curcumin II and curcumin III enriched compositions summarized above. As described and exemplified further herein, the invention provides that administration of such curcumin II and curcumin III enriched compositions elevates LDL receptor levels in a plurality of cells—which results in lower LDL levels in the cells and/or subject (which produces a number of therapeutic and health benefits).

According to further aspects of the present invention, LDL receptor-modulating therapeutic compositions are disclosed that comprise a curcumin composition that includes at least 15% (w/v) curcumin II, along with a pharmaceutically acceptable solvent, filler, or carrier. The invention provides that while the curcumin composition employed may comprise 15% (w/v) curcumin II, in certain preferred embodiments, the curcumin composition employed may comprise at least 30% (w/v) curcumin II. Still more preferably, the invention provides that the curcumin composition may comprise at least 50% (w/v) curcumin II, at least 70% (w/v) curcumin II or, even more preferably, at least 90% (w/v) curcumin II.

According to still further aspects of the present invention, LDL receptor-modulating therapeutic compositions are disclosed that include a curcumin composition that includes at least 5% (w/v) curcumin III and a pharmaceutically acceptable solvent, filler, or carrier. The invention provides that while the curcumin composition employed may comprise 5% (w/v) curcumin III, in certain preferred embodiments, the curcumin composition employed may comprise at least 30% (w/v) curcumin III. Still more preferably, the invention provides that the curcumin composition may comprise at least 50% (w/v) curcumin III, at least 70% (w/v) curcumin III or, even more preferably, at least 90% (w/v) curcumin III.

According to additional aspects of the invention, LDL receptor-modulating therapeutic compositions are disclosed that include a combination of the curcumin II and curcumin III enriched compositions described above.

According to additional aspects of the present invention, certain curcumin III enriched compositions described herein may be used to further modulate mitogen- and stress-activated protein kinase 1 (MSK1), which is a nuclear kinase that plays a significant role in transcription regulation (which produces a number of therapeutic and health benefits).

The above-mentioned and additional features of the present invention are further illustrated in the Detailed Description contained herein.

DETAILED DESCRIPTION OF THE INVENTION

Figure 1:
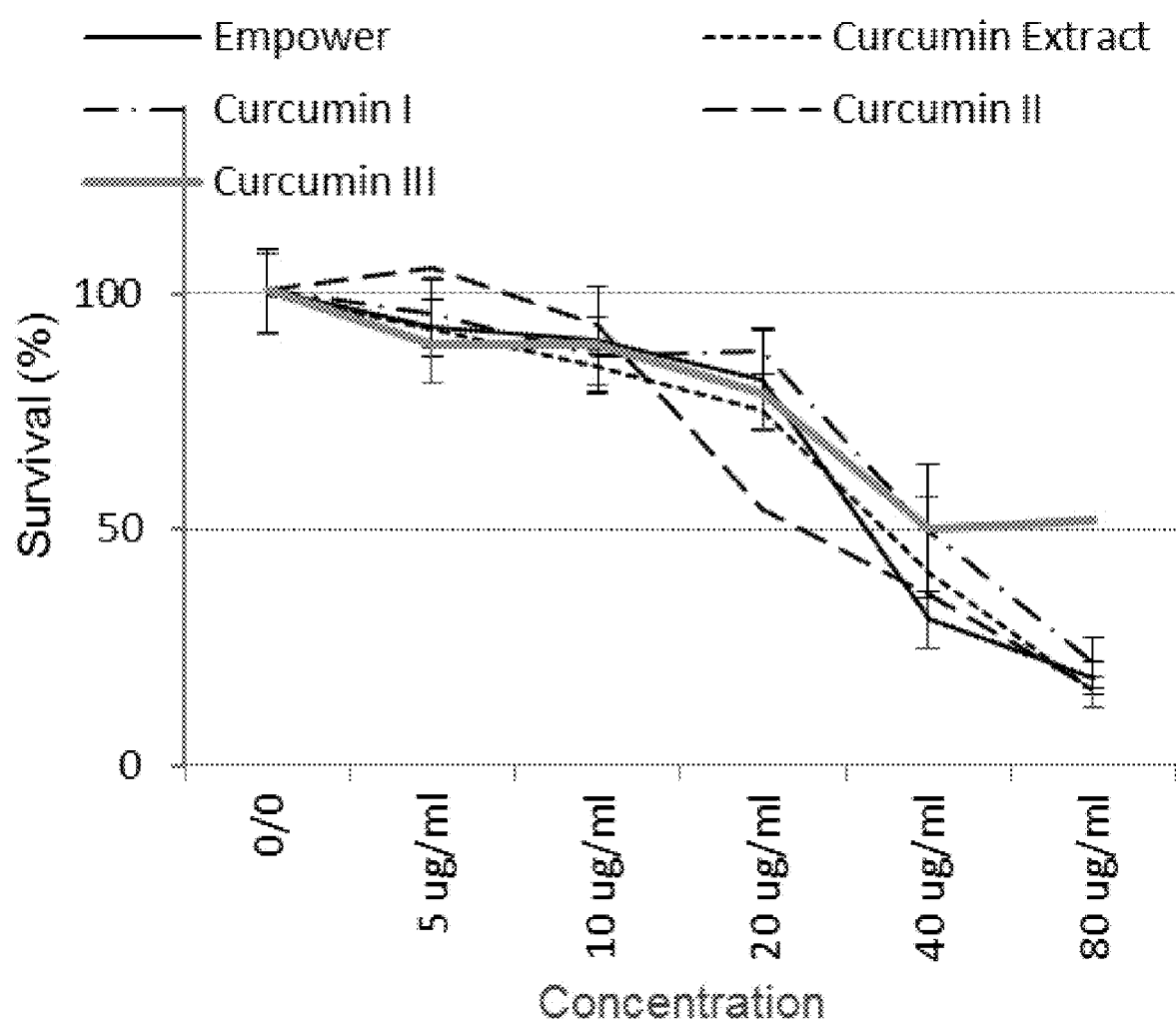
FIG. 1: MTT assay results demonstrating HEK293 cell survival of approximately 80% for all three curcuminoids (ranging from 20 to 22 µg/mL of the applicable curcuminoid).

The following will describe, in detail, several preferred embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used and made without departing from the scope and spirit of the invention.

According to certain preferred embodiments, the present invention includes certain curcumin-enriched compositions (and methods of using such compositions). More particularly, the present invention includes certain compositions that contain elevated and concentrated levels of (1) curcumin II (relative to the amount of curcumin II found in natural curcumin extract); (2) curcumin III (relative to the amount of curcumin III found in natural curcumin extract); or (3) a combination of curcumin II and curcumin III (relative to the amounts of curcumin II and curcumin III found in natural curcumin extract). Notably, the LDL receptor-modulating compositions described herein will preferably exclude curcumin I. The invention provides that such compositions can be used to increase low-density lipoprotein cholesterol (LDL) receptor expression levels in a plurality of cells (which, in turn, results in lower LDL levels in a subject and ameliorates a variety of associated health conditions and/or impart one or more associated health benefits).

In addition, the invention provides that certain curcumin III enriched compositions described herein may be used to modulate mitogen- and stress-activated protein kinase 1 (MSK1), which is a nuclear kinase that plays a significant role in transcription regulation. As described below, the invention provides that curcumin III (and not curcuminoids I and II) can be used to selectively and efficaciously inhibit cytoplasmic and nuclear MSK1 production, the inhibition of MSK1 serine$^{376}$ phosphorylation, and inhibition of the recruitment of MSK1 at inflammatory gene promotors. The curcumin III compositions described herein—and related methods of using such compositions—provide a major step in the transactivation regulation of downstream transcription factors that are key to cell survival and recruitment of inflammatory and immune system events. For example, as demonstrated in the Examples below, the ability of the curcumin III compositions described herein to inhibit MSK1 production (or otherwise significantly reduce MSK1 levels) indicates that such compositions may also (indirectly) be used to modulate NFkB (nuclear factor kappa-light-chain-enhancer of activated B cells)—the aberrant expression and transactivation of which has been linked to cancer, inflammation, and autoimmune diseases. The curcumin III compositions (and related methods) of the present invention provide improved efficacy, reliability, and drug target selectivity, relative to natural curcum in extracts.

A natural curcumin extract comprises a mixture of curcumin I, desmethoxycurcumin (curcumin II), and bisdemethoxycurcumin (curcumin III). The term curcumin refers to the principal curcuminoid in the Indian spice turmeric plant (a member of Zingiberaceae). The IUPAC name for the curcumin I molecule is (1E,6E)-1,7-Bis(4-hydroxy-3-methoxyphenyl)-1,6-heptadiene-3,5-dione. Although curcumin I may exist in several different tautomeric forms, the enol form is illustrated below:

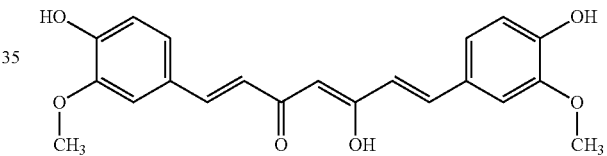

The IUPAC name for the desmethoxycurcumin (curcumin II) molecule is (1E,6E)-1-(4-Hydroxy-3-methoxyphenyl)-7-(4-hydroxyphenyl)hepta-1,6-diene-3,5-dione, and has the chemical structure shown below:

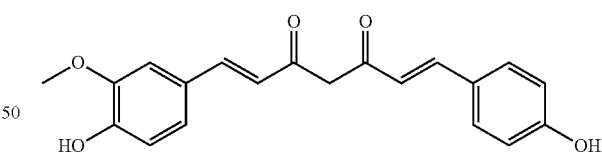

The IUPAC name for bis-desmethoxycurcumin (curcumin III) that is used in the compositions and methods of the present invention is (1E,6E)-1,7-bis(4-hydroxyphenyl)hepta-1,6-diene-3,5-dione, and has the chemical structure shown below:

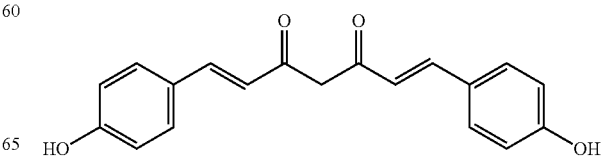

According to certain preferred embodiments, the invention provides that curcumin II and curcumin III may be extracted from turmeric plant rhizome (*Curcuma longa*) and subsequently concentrated to the desired levels. Alternatively, the invention provides that the curcumin II and curcumin III molecules may be chemically synthesized and used to formulate a therapeutic composition described herein. As explained below, the desired concentration of curcumin II is at least 15%, 30%, 50%, 70%, or 90% (w/v) curcumin II, while the desired concentration of curcumin III is at least 5%, 30%, 50%, 70%, or 90% (w/v) curcumin III.

According to certain preferred embodiments of the present invention, methods for increasing LDL receptor expression levels (and thereby lowering LDL) in a plurality of cells (and subject) are provided. In such embodiments, the methods include providing to the cells (or administering to a biological system that comprises a plurality of cells) an effective amount of a LDL receptor-modulating curcumin composition that is (1) at least 15% curcumin II; (2) at least 5% curcumin III; or (3) a combination of (1) and (2). According to additional preferred embodiments of the present invention, methods for inhibiting MSK1 serine$^{376}$ phosphorylation in a plurality of cells are provided. Such methods include providing to the cells (or administering to a biological system that comprises a plurality of cells) an effective amount of a curcumin composition that is at least 5% curcumin III.

The "effective amount" of a LDL receptor-modulating curcumin composition will preferably be sufficient to significantly increase LDL receptor expression levels (such as by at least 10% relative to a control cell line or, even more preferably, by at least 20% relative to a control cell line), to thereby reduce the amount of LDL in the target cells (and subject). Similarly, the "effective amount" of a MSK1-modulating curcumin composition will preferably be sufficient to significantly reduce the amount of MSK1 protein being expressed in the target cells (such as by at least 10% relative to a control cell line or, even more preferably, by at least 20% relative to a control cell line).

According to certain preferred embodiments of the present invention, methods for preventing and/or ameliorating the effects of certain diseases associated with high cholesterol (LDL) levels are provided. Such methods generally include providing to a subject an effective amount of the curcumin II and/or curcumin III enriched compositions described herein. Non-limiting examples of such diseases include cardiovascular diseases (including heart disease, stroke, peripheral vascular disease, atherosclerosis, arteriosclerosis, and serum LDL elevation), diabetes, and high blood pressure.

According to yet further preferred embodiments of the present invention, methods for preventing and/or ameliorating the effects of an adverse medical condition in which MSK1 is implicated are provided, including glucocorticoid-resistant inflammatory diseases and chemotherapy-resistant cancers. In such embodiments, the methods include providing to a subject a curcumin composition that is at least 5% curcumin III (or, alternatively, at least 30%, 50%, 70%, or 90% (w/v) curcumin III). According to certain related embodiments of the present invention, therapeutic compositions are provided that include a curcumin composition consisting of at least 5% (w/v) curcumin III; optionally, glucocorticoids; and a pharmaceutically acceptable solvent, filler, or carrier. As used herein, "glucocorticoids" refers to certain steroid hormones that are known to bind to glucocorticoid receptors (RCEs). Non-limiting examples of glucocorticoids include: cortisol, cortisone, prednisone, prednisolone, methylprednisolone, dexamethasone, betamethasone, triamcinolone, beclometasone, fludrocortisone, deoxycorticosterone, and aldosterone. In the foregoing embodiments of the invention, while the curcumin composition employed may comprise 5% (w/v) curcumin III, in certain preferred embodiments, the curcumin composition employed may comprise at least 30% (w/v) curcumin III. Still more preferably, the invention provides that the curcumin composition may comprise at least 50% (w/v) curcumin III, at least 70% (w/v) curcumin III or, even more preferably, at least 90% (w/v) curcumin III—depending on the desired potency.

The invention provides that the concentrated forms of the curcumin III based compositions (and methods of using such compositions) described herein exhibit many benefits—for humans, canines, cats and equine. First, as demonstrated below and described herein, the invention provides that elevated levels of curcumin III will selectively inhibit MSK1 production, which thereby produces desirable anti-inflammatory activity. In addition, the invention provides that the compositions and methods described herein may be used for therapeutic nutrition; anti-inflammatory therapy for autoimmune disease and other chronic and acute inflammatory ailments; treatment of pain, swelling and inflammation; nutritional supplementation; superbug treatments; and anti-microbial, antifungal, antibacterial, and antiviral therapies.

Still further, according to certain additional embodiments, the present invention encompasses therapeutic compositions (and methods of use thereof) that include a curcumin composition consisting of at least 15% curcumin II, along with a pharmaceutically acceptable solvent, filler, or carrier. In such embodiments, as described above, the curcumin II-enriched compositions can be used to increase LDL receptor expression levels and thereby lower LDL levels in target cells and/or a subject. Indeed, as shown in the Example below, curcumin II-enriched and curcumin III-enriched compositions can be used to increase LDL receptor expression levels (and, therefore, lower LDL levels in target cells and/or a subject).

In certain specific embodiments, the compositions and methods described herein may also be used to ameliorate the effects of autoimmune diseases (and other inflammatory conditions), such as rheumatoid arthritis, colitis, non-specific inflammatory bowel diseases, crohn's disease, lupus, multiple sclerosis, psoriasis, type-I diabetes, diabetes, myocarditis, thyroiditis, uveitis, systemic lupus erythromatosis, myasthenia and gravis. Furthermore, the compositions and methods described herein may be used to ameliorate the effects of autoimmune syndromes, such as the sources of immune-mediated inflammation (which can promote chronic inflammation, Alzheimer's, asthma, allergies, obesity, chronic fatigue, fibromyelia, premature aging, and general memory impediments). Still further, the compositions and methods may be used for the purpose of performance enhancement; recovery from physical exercise; and to help neutralize lactic acid, oxidation and associated inflammatory responses to workload to improve recovery rate, anabolism, reduce post-workout soreness and associated fatigue (and allow for repeat workout sessions earlier than could otherwise be executed in typical workout and training cycles).

The invention provides that the compositions described herein may be administered in any desired and effective manner, e.g., as pharmaceutical compositions or nutritional supplements for oral ingestion. More particularly, for example, pharmaceutically acceptable compositions or nutritional supplements of the invention may comprise one or more of the compositions described herein with one or more acceptable carriers. Regardless of the route of administration selected, the compositions may be formulated into acceptable dosage forms by conventional methods known to those of skill in the art. For example, acceptable carriers include, but are not limited to, sugars (e.g., lactose, sucrose, mannitol, and sorbitol), silicon dioxide, starches, cellulose preparations (such as microcrystalline cellulose), calcium phosphates (e.g., dicalcium phosphate, tricalcium phosphate and calcium hydrogen phosphate), sodium citrate, water, aqueous solutions, alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes, paraffins, silicones, talc, silicylate, etc.

Each acceptable carrier used in a pharmaceutical composition or nutritional supplement of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The pharmaceutical compositions and nutritional supplements of the invention may, optionally, contain additional ingredients and/or materials commonly used in pharmaceutical compositions and/or nutritional supplements. Such ingredients and materials include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxy methyl cellulose and sodium carbonate; (5) solution retarding agents, such as paraffin; (6) absorption accelerators, such as quaternary ammonium compounds; (7) wetting agents, such as cetyl alcohol and glycerol monosterate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monsterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; (28) vitamins and minerals; (29) proteins that carry therapeutic or nutritional benefits, such as whey protein and other milk-derived proteins; and (30) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutical compositions and nutritional supplements suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, or a paste. These formulations may be prepared by methods known in the art, e.g., by means of conventional pan-coating, mixing, granulation or lyophilization processes.

Solid dosage forms for oral administration (capsules, tablets, pills, powders, granules and the like) may be prepared by mixing the active ingredient(s) with one or more acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as capsules, pills and granules, may optionally be scored or prepared with coatings and shells, such as enteric coatings and other coatings well known in the art. The tablets, and other solid dosage forms, may also be formulated so as to provide slow or controlled release of the active ingredient therein. They may be sterilized by, for example, filtration through a bacteria-retaining filter. These compositions may also optionally contain opacifying agents that release the active ingredient only, or preferentially, in a certain portion of the gastrointestinal tract, optionally, in a delayed manner. The active ingredient can also be in a microencapsulated form.

Liquid dosage forms for oral administration include acceptable emulsions, microemulsions, solutions, suspensions, syrups, and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

EXAMPLES

Example 1—MTT Assay. MTT (3-[4,5-dimethylthiazol-2-yl]-2,5-diphenyltetrazolium bromide) assays are routinely used to measure cell viability and survival. In this Example, cytotoxicity of curcuminoids on two cell types—HEK293T and BV2 microglia—was measured. The MTT assay quantifies the formazan production by live cells from the tetrazolium ring cleavage of MTT. Reduction of MTT is directly proportional to metabolic activity and therefore relatable to cell viability and survival. A first MTT assay was performed on HEK293T cells in a 96-well plate requiring $3\times10^4$ cells per well. The MTT assay was also performed using BV2 microglia cells, pursuant to the same protocol (utilizing a 96-well plate requiring $3\times10^4$ cells per well). Dimethyl sulfoxide (DMSO) was used in the test drug (curcuminoid) preparation at 0.2%. The MTT assay was used to measure the health of the cells in culture with various treatment concentrations of various curcumin preparations.

Figure 2:
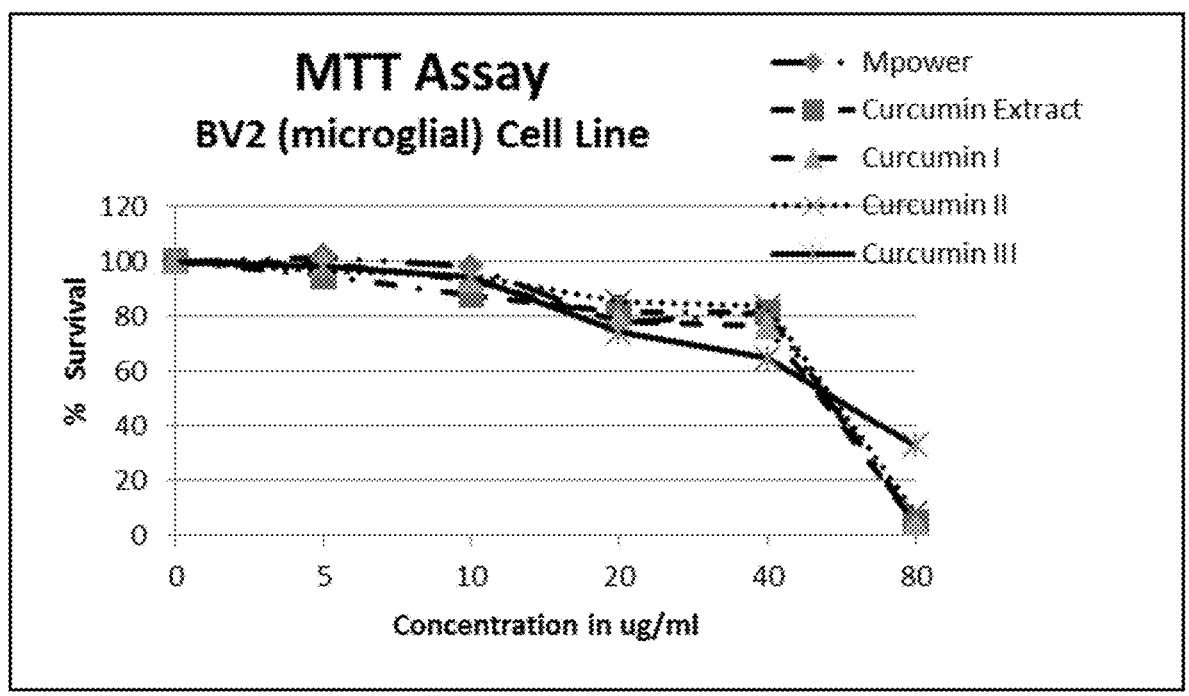
FIG. 2: MTT assay results demonstrating BV2 cell survival of approximately 80% for all three curcuminoids (ranging from 20 to 22 µg/mL of the applicable curcuminoid).

As shown in FIG. 1 (HEK293T cells) and FIG. 2 (BV2 microglia), the MTT assay results revealed that the selected cell models are relatively resilient to the curcuminoid drugs at the tested concentrations. Cell survival was shown to begin to decline below 80% survival at a drug (curcuminoid) concentration around 40 µg/ml. Accordingly, a final test concentration of 22 µbg/ml was selected and employed in the Examples that follow.

Example 2—Western Blot Analysis of Cytoplasmic and Nuclear MSK1 Levels. Western blot analysis was performed in multiple varying formats before optimization was achieved. The BV2 microglia cell line was cultured in Dulbecco's Modified Eagle's Medium (DMEM)—complete medium. The complete medium consisted of DMEM, 1% Ampicillin, and 10% Fetal Bovine Serum (FBS). BV2 microglia cells, at a cell count of approximately $2\times10^6$, were seeded in each well (6 wells per plate) with 2.0 ml complete medium and cultured overnight in a ThermaForma HepaFilter Series II Coe Incubator at 37° Celsius. Upon establishing confluence, subconfluent cells were washed out and the wells were prepared with drug pre-treatment after overnight incubation.

The test drugs (curcuminoids) were procured as follows: curcumin I research standard (03926) (ChromaDex Irvine, Calif. USA) (97.7% purity); curcumin II research standard (04230) (ChromaDex Irvine, Calif. USA) (97.3%); curcumin III research standard (B6938) (Sigma-Aldrich St. Louis, Mo., USA) (97.7% purity); curcumin extract (curcumin I—77.7%, curcumin II—16.9%, curcumin III—0.9%) research standard (03928) (ChromaDex Irvine, Calif. USA) (95.3% purity); and Lipopolysaccharide (LPS) from *E. Coli* (L2630) (Sigma-Aldrich St. Louis, Mo., USA).

Curcuminoids are not soluble in aqueous medium due to their hydrophobic characteristic. However, curcuminoid extracts are soluble in polar organic solvents, such as DMSO and acetone. In this Example, each curcuminoid preparation was first dissolved in DMSO. DMSO was used in the drug preparation at 0.2%. The drug/DMSO solution was subsequently dissolved in DMEM to achieve a final drug concentration for each curcuminoid preparation tested—22.0 µg/ml curcuminoid. The DMEM/drug solution was used to replace the culture DMEM well medium and incubated for 30 minutes at 37-degrees Celsius in a ThermaForma incubator. At 31 minutes, lipopolysaccharide (LPS at 1.0 µl/ml final well concentration) induction of the cells was executed, except for the DMSO-only well to stimulate cell response amidst drug pre-treatment and without drug treatment.

The plates were then incubated for another 30 minutes after LPS stimulation. Upon removal from incubation, the cell medium was carefully removed and cells were washed, scraped, and collected with phosphate-buffered saline (PBS). Using a ThermoFisher Scientific NE-PER Nuclear and Cytoplasmic Extraction Kit (obtained from ThermoFisher Scientific Burlington, Ontario Canada), the cells were lysed and the cytoplasmic and nuclear protein fractions were collected and separated with the intention of probing each fraction for subcellular changes in cytoplasmic and nuclear proteins (as described further below).

Total protein concentration for each fraction was determined using a Bio Rad Protein Assay that is based on the Bradford Assay (dye-binding method). The total protein concentration determination was made prior to test sample preparation for gel electrophoresis execution (described below). The protein concentration colorimetric assay kit was purchased from Bio Rad Laboratories Canada Ltd. (Montreal, Quebec Canada). Each test sample was then prepared for loading and subjected to gel electrophoresis (SDS-PAGE) using a BioRad stain free gel system (Catalog No. 161-0181) and subsequently transferred/blotted to a nitrocellulose membrane (ThermoFisher Scientific Product No. 88018), blocked, and prepared for primary antibody treatment for each target.

The targets analyzed in the Western Blot included NFkB-p65 and its nucleocytoplasmic translocation, as well as kinases (including MSK1) and their covalent modifications upstream of and involved in the regulation of NFkB. Antibodies against NFkB-p65 (Ab16502) were procured from Abcam Inc. (Toronto, Ontario, Canada) as a primary antibody to probe for total NFkB-p65 levels in both nuclear and cytoplasmic fractions. Antibodies against phosphorylated NFkB p65 at serine 276 (sc-101749) were procured from Santa Cruz Biotechnologies Inc. Antibodies against MSK1 total protein (SAB4503597) were procured from Sigma-Aldrich Company (St. Louis, Mo., USA), and antibodies against phosphorylated MSK1 at serine 376 (SAB4504475) were also procured from Sigma-Aldrich Company. The antibodies were used to probe for both nuclear and cytoplasmic levels of each protein and its modified state—the phosphorylation site which determines its activated (or most active) state. Secondary antibody conjugated to a horseradish peroxidase (HRPO) enzyme was used to detect the bound primary antibodies. Following incubation, washing, and substrate activation of the HRPO-labeled secondary antibody, the membrane was scanned using a Bio Rad ChemDoc MP Imaging System (and the detected Western Blot bands were quantified using Image J Software).

Figure 3:
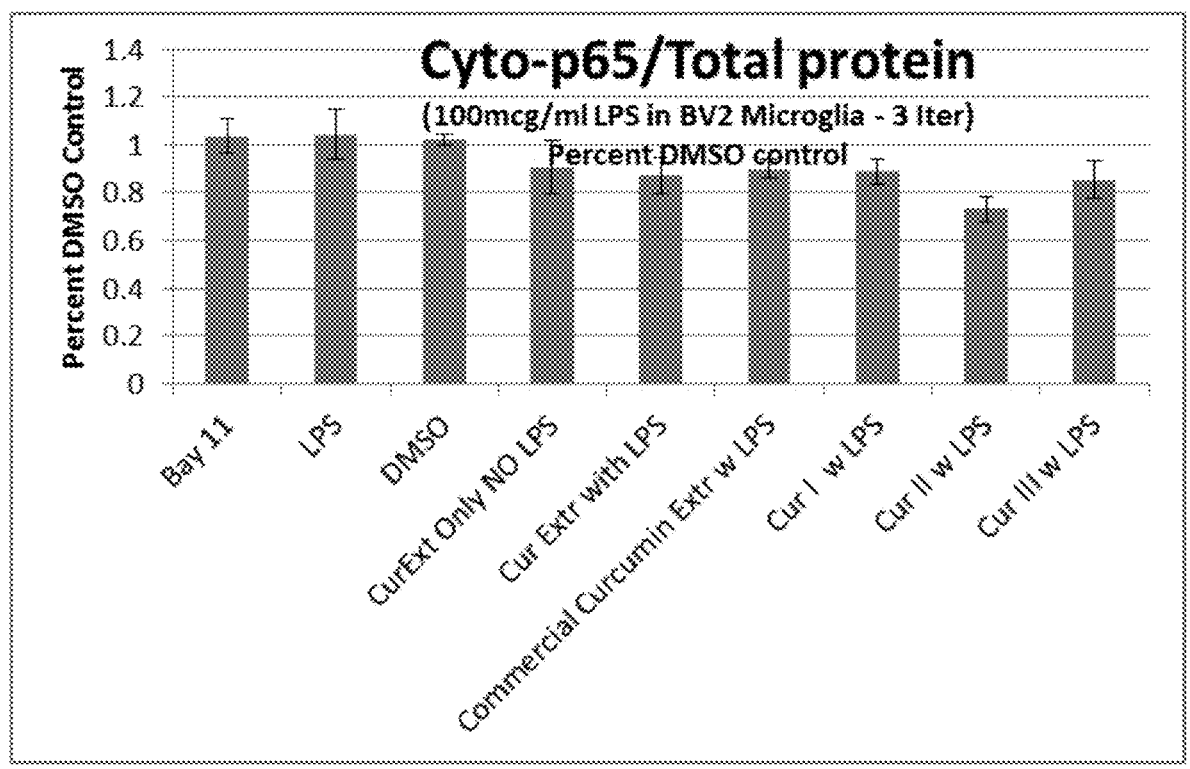
FIG. 3: measurements of cytoplasmic NFkB-p65 protein levels relative to total protein concentration in BV2 cell lines provided with curcumin extract, curcuminoid I, curcuminoid II, curcuminoid III, and controls.
Figure 4:
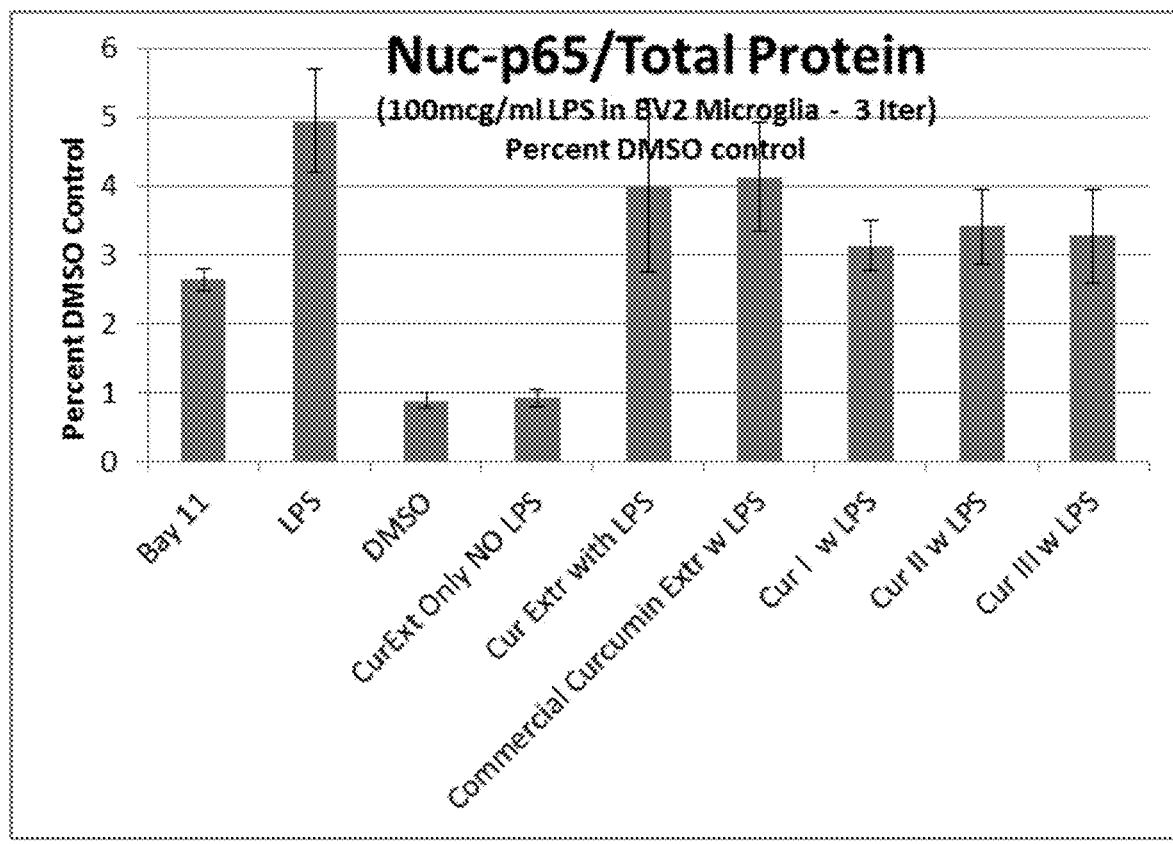
FIG. 4: measurements of nuclear NFkB-p65 protein levels relative to total protein concentration in BV2 cell lines provided with curcumin extract, curcuminoid I, curcuminoid II, curcuminoid III, and controls.
Figure 5:
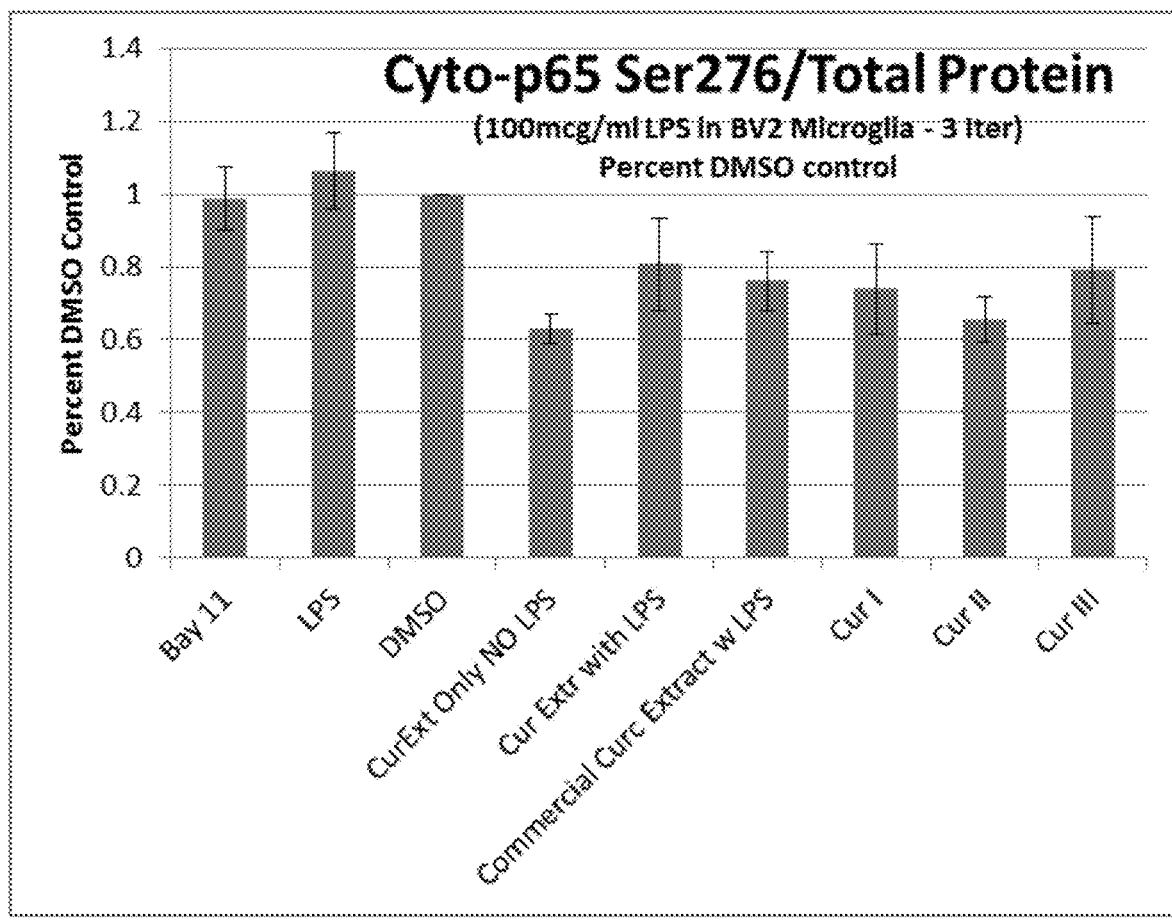
FIG. 5: measurement of cytoplasmic NFkB p65 that is phosphorylated at the serine 276 phosphosite, relative to total protein concentration in BV2 cell lines provided with curcumin extract, curcuminoid I, curcuminoid II, curcuminoid III, and controls.
Figure 6:
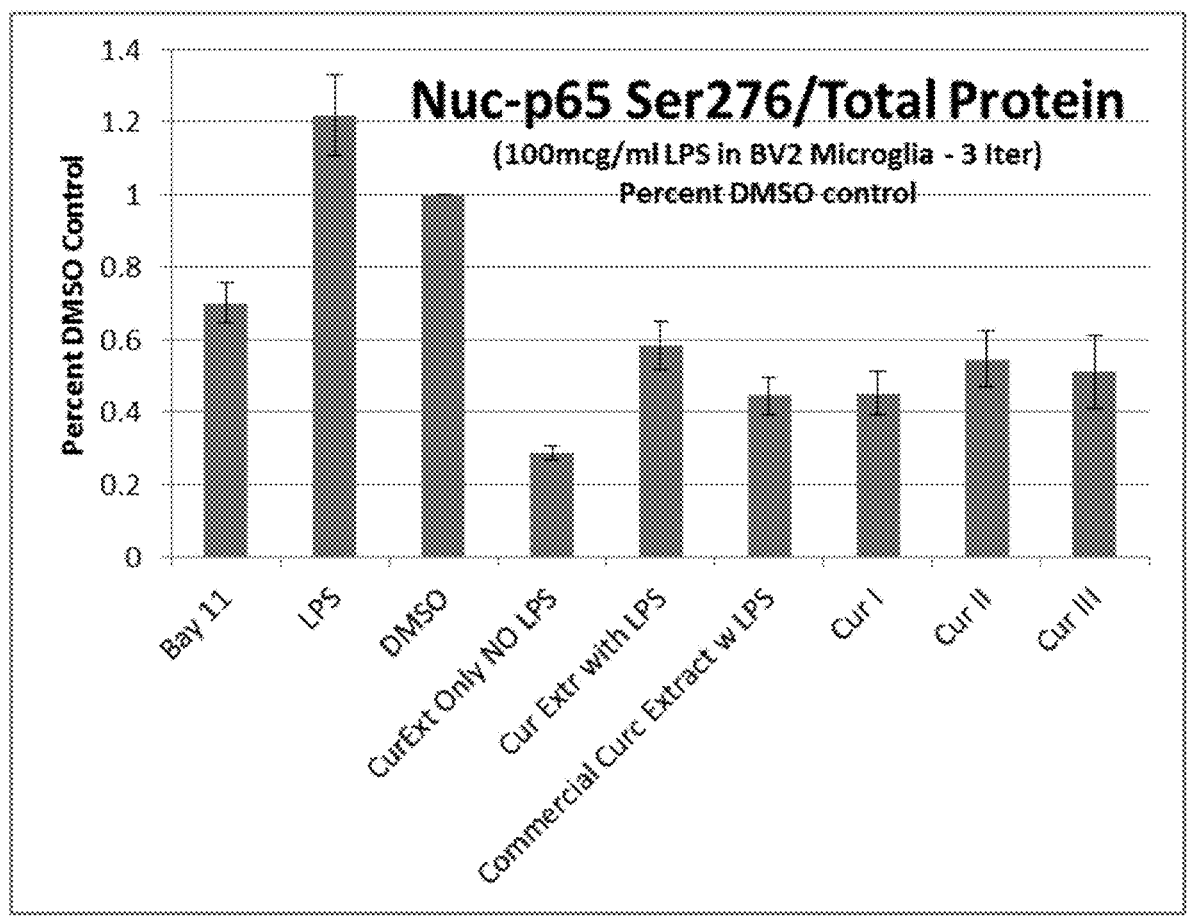
FIG. 6: measurement of nuclear NFkB p65 that is phosphorylated at the serine 276 phosphosite, relative to total protein concentration in BV2 cell lines provided with curcumin extract, curcuminoid I, curcuminoid II, curcuminoid III, and controls.

FIG. 3 shows the Western Blot measurements of cytoplasmic NFkB-p65 protein levels relative to total protein concentration, in BV2 cell lines provided with curcumin extract, curcuminoid I, curcuminoid II, curcuminoid III, and controls. FIG. 4 shows the Western Blot measurements of nuclear NFkB-p65 protein levels relative to total protein concentration, in BV2 cell lines provided with curcumin extract, curcuminoid I, curcuminoid II, curcuminoid III, and controls. FIG. 5 shows the Western Blot measurements of cytoplasmic NFkB-p65 phosphorylated at serine 276 relative to total protein concentration, in BV2 cell lines provided with curcumin extract, curcuminoid I, curcuminoid II, curcuminoid III, and controls. FIG. 6 shows the Western Blot measurements of nuclear NFkB-p65 that is phosphorylated at serine 276 relative to total protein concentration, in BV2 cell lines provided with curcumin extract, curcuminoid I, curcuminoid II, curcuminoid III, and controls.

The cytosolic and nuclear NFkB-p65 data (FIGS. 3 and 4) reveal that nucleotranslocation is not significantly inhibited by curcumin extract, curcumin I, curcumin II, nor curcumin III. As shown in FIGS. 5 and 6, however, curcumin extract and each of the curcuminoids—I, II, and III—moderately inhibit NFkB-p65 serine$^{276}$ phosphorylation to significantly inhibit p65-p50 transactivation, while nucleotranslocation is relatively low in this same context. Indeed, the more robust inhibition of NFkB-p65 serine$^{276}$ phosphorylation of the transcription factor's Transactivation Domain II reveals a relevant mechanism by which each of the curcuminoids inhibits p65p50 transactivation and downstream immune and inflammatory activity. These data show that each curcuminoid, including the curcumin extract, comparably inhibits this key site phosphorylation to downregulate immune system and inflammatory activity. This demonstrates an ability of curcuminoid drugs to treat cells that may feature pathological constitutive p65-p50 nucleotranslocation, which is a common pathological feature of cancer and chronic inflammatory conditions (including autoinflammatory and autoimmune conditions).

Figure 7:
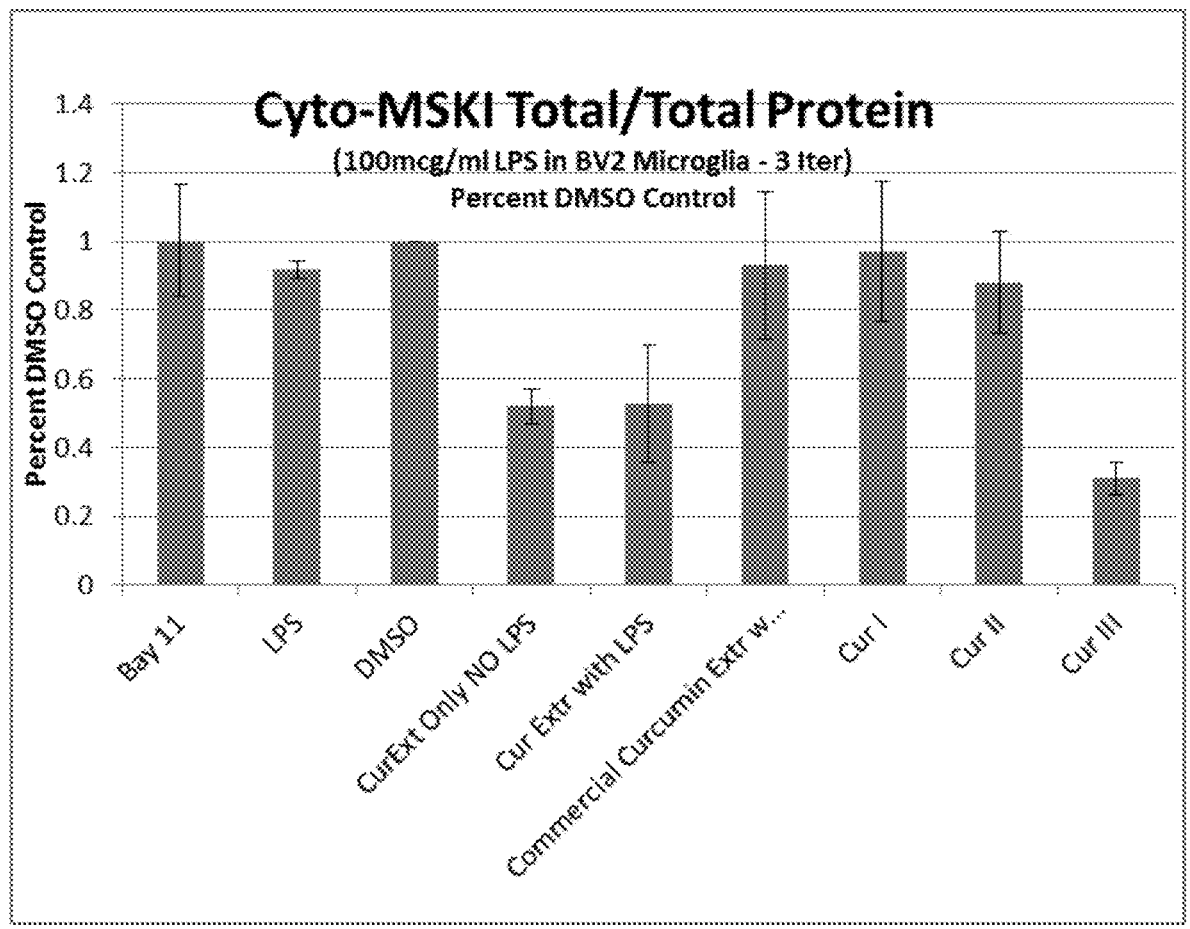
FIG. 7: measurement of cytoplasmic MSK1 protein levels relative to total protein concentration in BV2 cell lines provided with curcumin extract, curcuminoid I, curcuminoid II, curcuminoid III, and controls.
Figure 8:
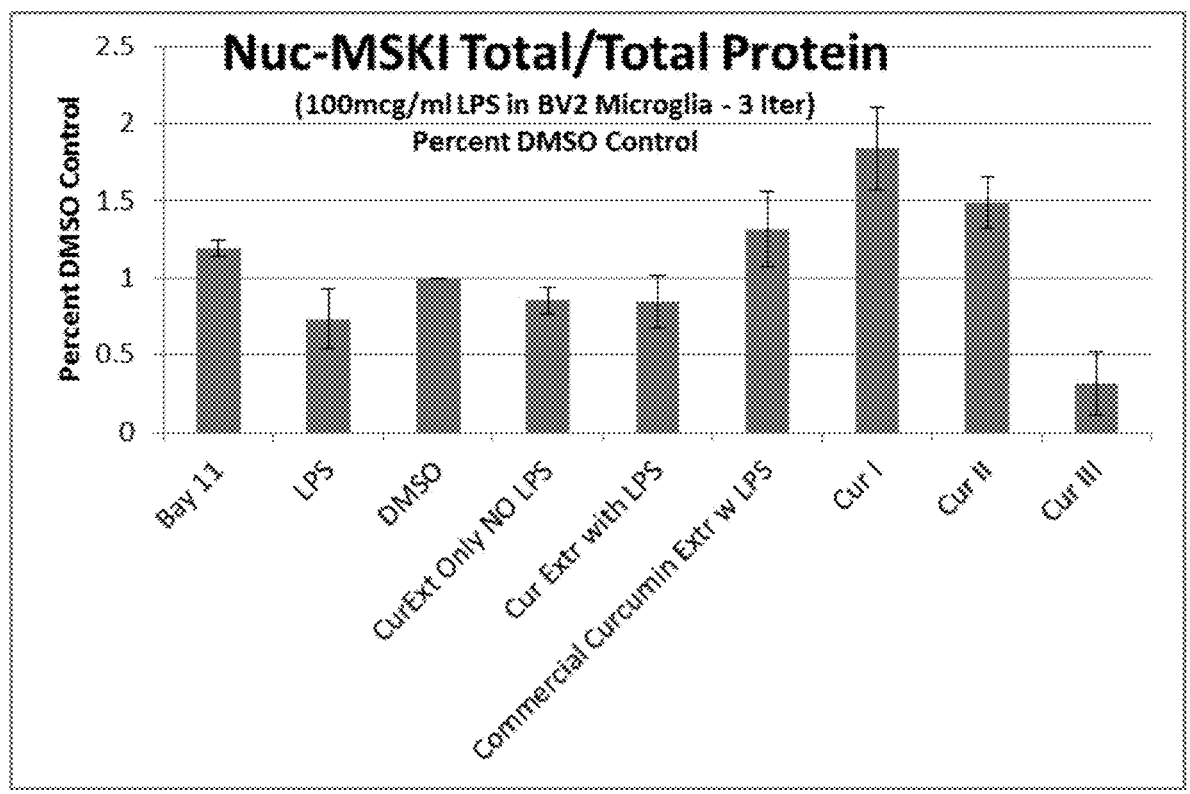
FIG. 8: measurement of nuclear MSK1 protein levels relative to total protein concentration in BV2 cell lines provided with curcumin extract, curcuminoid I, curcuminoid II, curcuminoid III, and controls.
Figure 9:
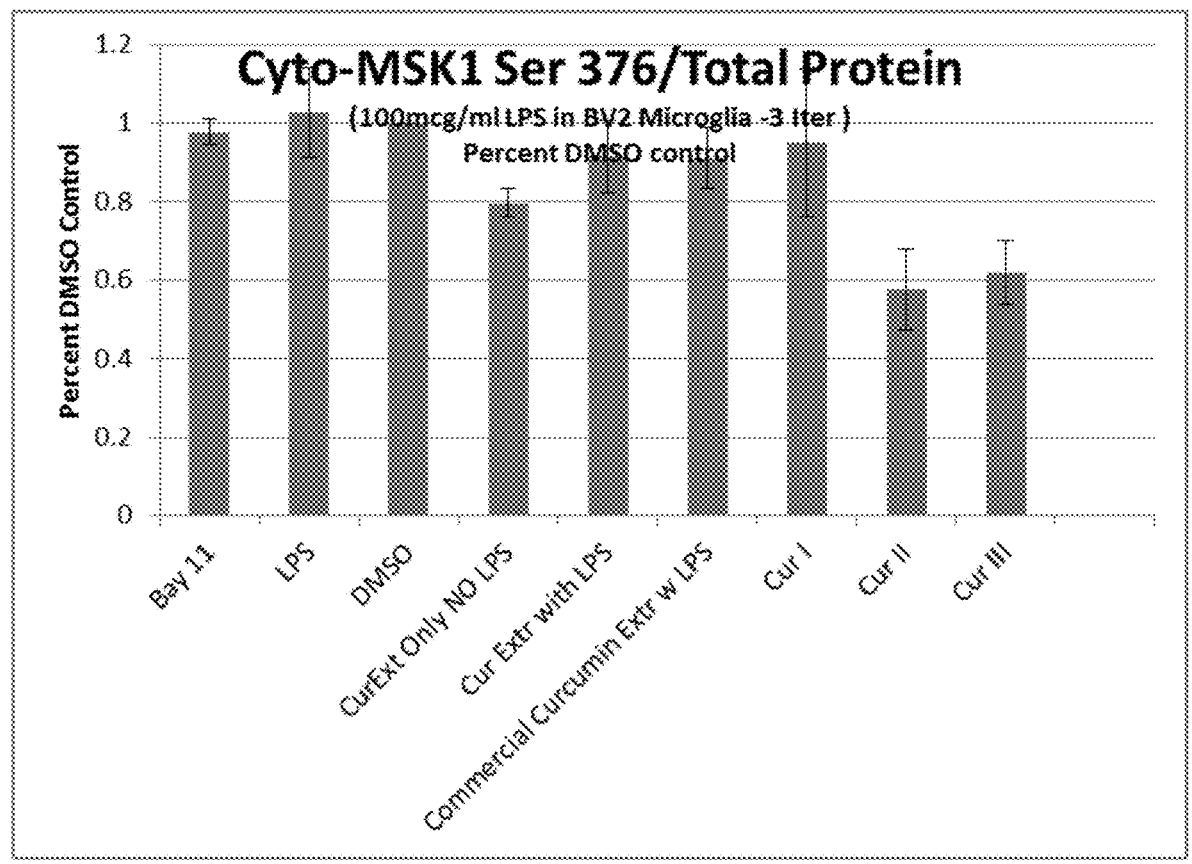
FIG. 9: measurement of cytoplasmic MSK1 that is phosphorylated at the serine 376 phosphosite, relative to total protein concentration in BV2 cell lines provided with curcumin extract, curcuminoid I, curcuminoid II, curcuminoid III, and controls.
Figure 10:
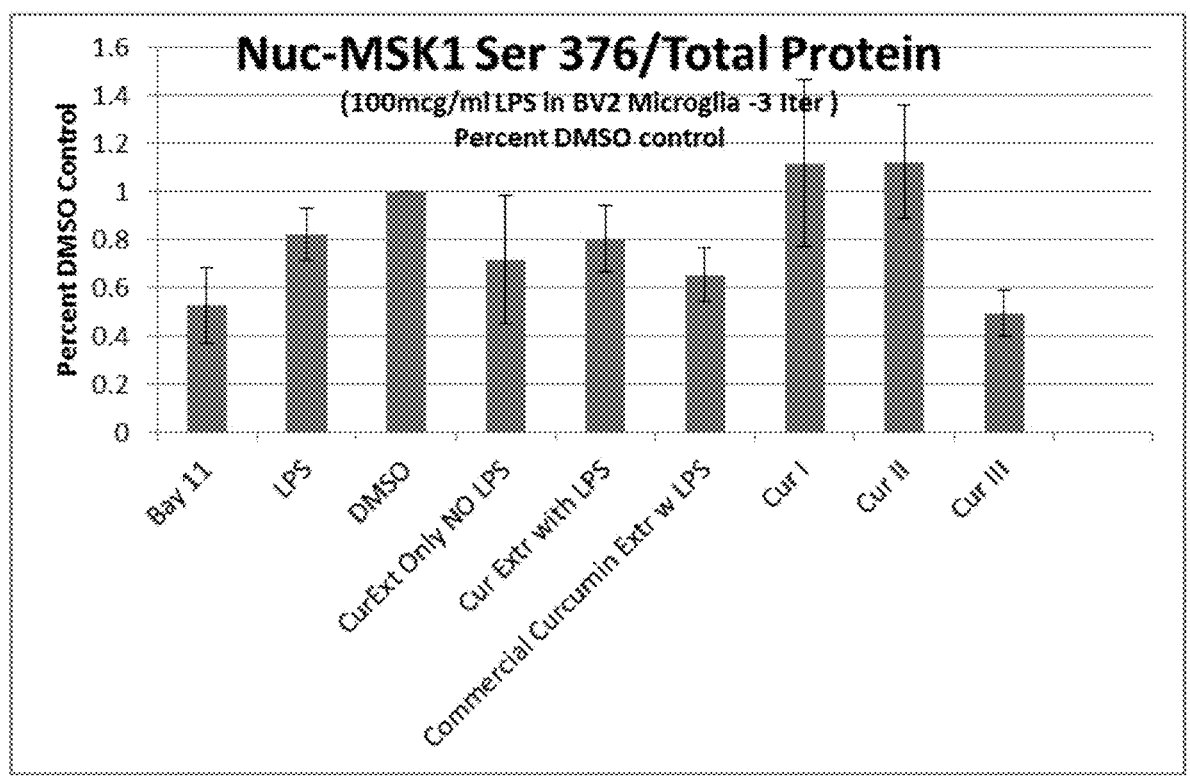
FIG. 10: measurement of nuclear MSK1 that is phosphorylated at the serine 376 phosphosite, relative to total protein concentration in BV2 cell lines provided with curcumin extract, curcuminoid I, curcuminoid II, curcuminoid III, and controls.

Furthermore, and perhaps even more profound, inhibition of MSK1 protein levels was revealed by Western Blot analysis (FIGS. 7 and 8). More specifically, it was found that curcumin III—but not curcumin extract, curcumin I or curcumin II—significantly inhibited and downregulated MSK1 protein levels in both the cytoplasm and the nucleus (FIGS. 7 and 8). The Western Blot analysis summarized in FIGS. 7 and 8 shows curcumin III selectively inhibits MSK1 expression, while certain other curcuminoids (namely, curcumin II) were only shown to inhibit MSK1 serine 376 phosphorylation (FIGS. 9 and 10).

As illustrated in this Example (and in FIGS. 7 and 8), the inventor discovered that curcumin III displays independent and additional pharmacology leading to MSK1 protein downregulation, and that its influence on MSK1 is likely independent and more selectively focused on MSK1 (and not upstream of the kinase). This Example shows the inhibitory influence that is selectively imparted by isolated and enriched curcumin III compositions (and not the other curcuminoids). In addition, the Examples show inhibition of MSK1 expression is not conveyed by typical curcumin extracts—likely because the curcumin III levels in such natural extracts is inherently too low to achieve such activity (a typical natural curcumin extract contains low levels of curcumin III, often about 0.2%-1% curcumin III).

Example 3—Effects of Curcumin II and Curcumin III on LDL Receptor Expression. A HepG2 cell line was used in this Example to observe the effects of three different curcuminoids (curcumin I, II and III), at 22 µg/mL concentration, on LDL receptor expression levels. To prepare each curcuminoid solution, 2.2 mg of curcuminoid powder (ChromaDex Irvine, Calif. USA) was measured and dissolved in 100 µL of DMSO to prepare a stock concentration of 22 mg/mL. 10 µL of the stock solution was added to 10 mL of MEM media (Sigma-Aldrich St. Louis, Mo., USA) to prepare a final test concentration of 22 µg/mL.

HepG2 cells were cultured on a tissue culture dish (58 cm$^2$) with MEM media (10% FBS, 1% Antibiotic-antimycotic) until the cells were 90% confluent. For each curcuminoid, three biological replicates were plated. On the day of the treatment, existing media were replaced with 2 mL of 22 µg/mL curcuminoid containing MEM media in the respective wells. After 30 minutes of incubation, the cells were washed twice with cold PBS. Next, 100 µL of lysis buffer (RIPA 1920 µL and protease inhibitor cocktail (25×) 80 µL) was added to each well. A scrapper was used to scrap the cells into the lysis buffer and the samples were collected in a 0.5 mL pre-chilled Eppendorf tube. Each sample was sonicated for 30 seconds followed by centrifugation at 13000 RPM at 4° C. for 30 minutes. The supernatant was then used for protein quantification (using a BioRad DC Protein Assay Kit).

For Western blotting, 15 µg of samples were loaded onto a 1% acrylamide gel (BioRad) and subject to electrophoresis for 50 minutes at 200V. The samples were then transferred (blotted) to a nitrocellulose membrane (GE Healthcare) using a wet transfer method at 90V for 1 hour. The membranes were subsequently blocked in 5% blocking solution (5% skim milk in 0.01% TBS-T) for 1 hour. A rabbit polyclonal primary antibody (Abcam) against LDL receptor (1:500) and a rabbit polyclonal primary antibody (Abcam) against actin (1:5000) was applied and incubated with the membranes overnight at 4° C. Following three 5 minutes washes with TBS-T, a tagged goat anti-rabbit secondary antibody was applied and incubated at a 1:10,000 concentration for 1 hour at room temperature. The membranes were subsequently scanned with Quantity one scanner. The scan images were analyzed using ImageJ software. A two-tail, paired students T-test was performed to analyze the data.

Figure 11:
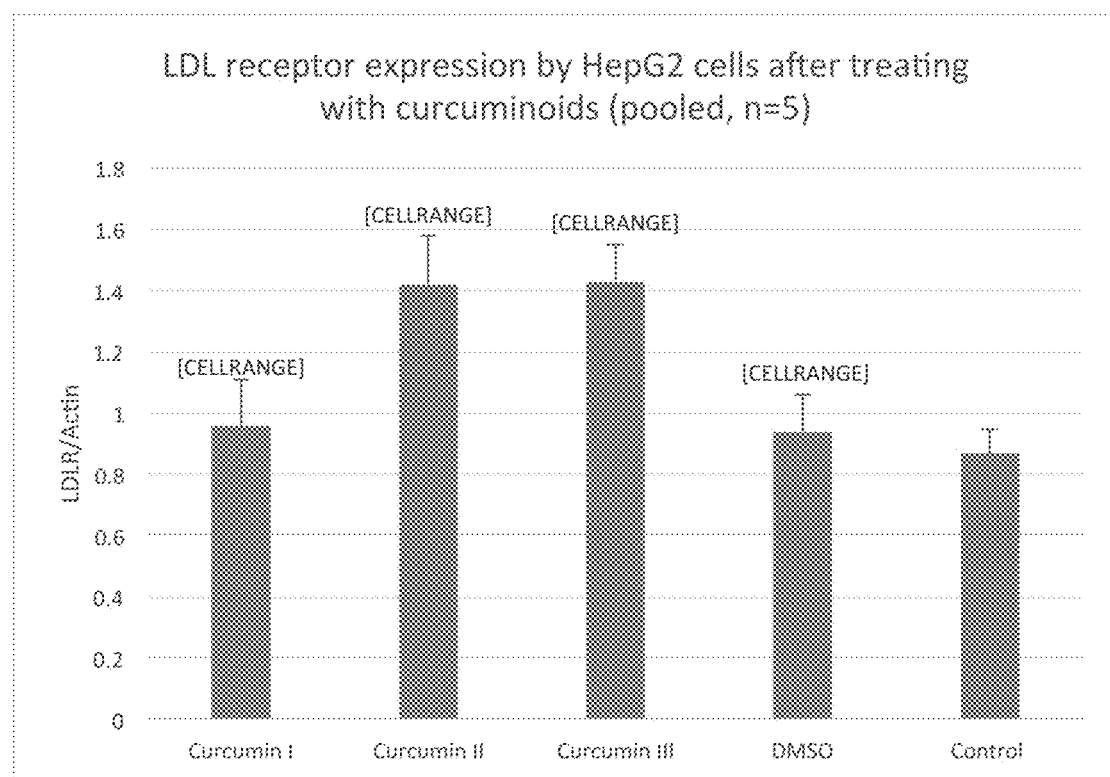
FIG. 11: measurement of LDL receptor expression levels in HepG2 cells after treatment with 22 μg/mL curcuminoid I, curcuminoid II, curcuminoid III, and controls.

The data were analyzed as a ratio of LDL receptor expression standardized to the actin housekeeping gene. As shown in FIG. 11, the presence of both curcumin II (p=0.022964) and curcumin III (p=0.008044) resulted in significantly higher expression of LDL receptor levels compared to control (untreated) cells (the error bar shown in FIG. 11 represents the standard error of the mean and p-values represent Student T-test analysis (for each sample, n=3)). In contrast, the presence of curcumin I (p=0.643059) and DMSO (p=0.607996) resulted in about the same expression of LDL receptor levels as observed with control treatment. The data show that curcumin II and III exhibit about the same efficacy in enhancing expression of LDL receptor.

Figure 12:
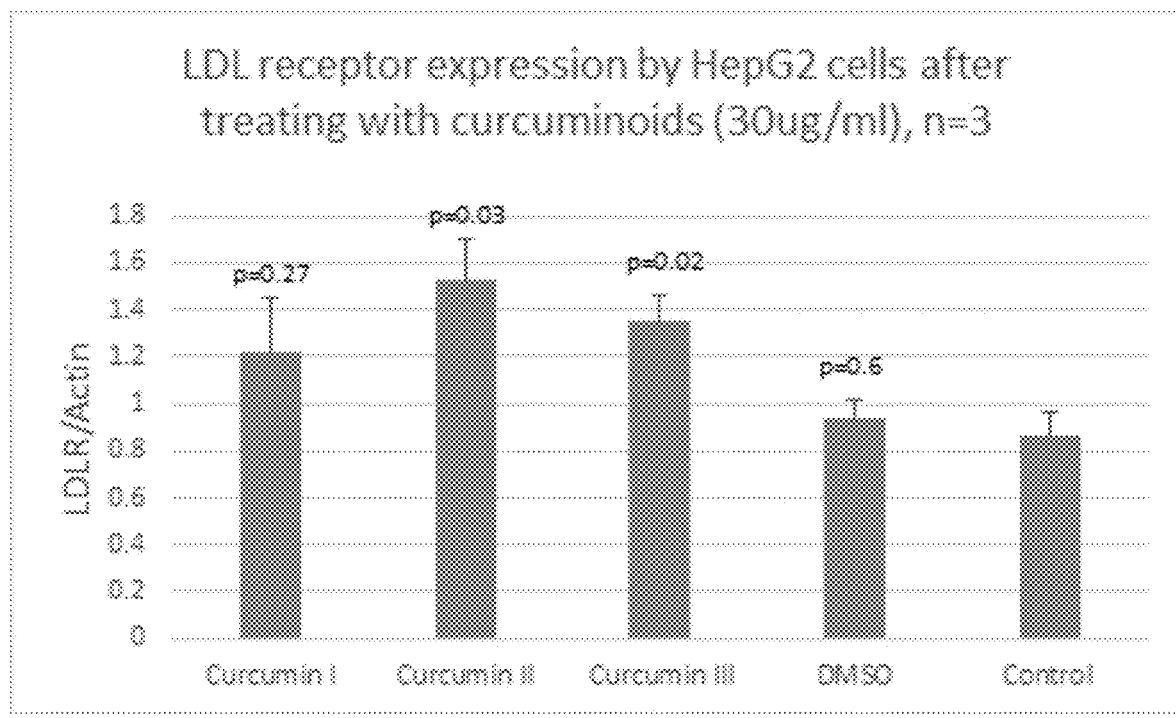
FIG. 12: measurement of LDL receptor expression levels in HepG2 cells after treatment with 30 μg/mL curcuminoid I, curcuminoid II, curcuminoid III, and controls.

The effects of the three different curcuminoids (curcumin I, II and III) on LDL receptor expression levels were confirmed in a subsequent experiment, using the same methodology described above, but testing each curcuminoid at 30 µg/mL concentration (instead of 22 µg/mL). As shown in FIG. 12, curcumin II and curcumin III both resulted in significantly higher expression of LDL receptor levels compared to control (untreated) cells.

Example 4—Curcumin Formulation One. The following describes a non-limiting example, but a preferred embodiment, of a composition that is encompassed by the present invention. More particularly, the composition includes 30-40% curcumin I (such as about 35% curcumin I); 9-11% curcumin II (such as about 10% curcumin II); and 45%-55% curcumin III (such as about 50% curcumin III). Preferably, such composition is formulated into a capsule that can be administered orally. In such embodiments, the capsule may comprise additional fillers and agents, such as a vegetable capsule (hydroxypropyl methylcellulose), water, microcrystalline cellulose, magnesium stearate, and silicon dioxide. In such embodiments, a subject may consume 1-3 capsules per day (and each dose may include, but is not limited to, about 1131 mg of the total composition), to achieve the desired effects described herein.

Example 5—Curcumin Formulation Two. The following describes another non-limiting example, and another preferred embodiment, of a composition that is encompassed by the present invention. More particularly, the composition includes 45-55% curcumin I (such as about 50% curcumin I); 10-20% curcumin II (such as about 15% curcumin II); and 20%-40% curcumin III (such as about 30% curcumin III). As with the Example above, such composition is preferably formulated into a capsule that can be administered orally. Likewise, in such embodiments, the capsule may comprise additional fillers and agents, such as a vegetable capsule (hydroxypropyl methylcellulose), water, magnesium stearate, and silicon dioxide. In such embodiments, a subject may consume 1-3 capsules per day (and each dose may include, but is not limited to, about 1131 mg of the total composition), to achieve the desired effects described herein.

Example 6—Curcumin Formulation Three. The following describes another non-limiting example, and yet another preferred embodiment, of a composition that is encompassed by the present invention. More particularly, the composition includes (or consists of) natural curcumin extract, which is supplemented with additional (and preferably purified) curcumin III, such that the final curcumin III concentration is greater than 5% (w/v). In certain embodiments, the final curcumin III concentration is at least 30% (w/v) curcumin III or, more preferably, at least 50% (w/v) curcumin III. As with the other embodiments described herein, the formulation may be formulated as a capsule, and the capsule may (optionally) comprise additional fillers and agents, such as a vegetable capsule (hydroxypropyl methylcellulose), water, magnesium stearate, and silicon dioxide. In such embodiments, a subject may consume 1-3 capsules per day (and each dose may include, but is not limited to, about 1131 mg of the total composition), to achieve the desired effects described herein.

Example 7—Curcumin Formulation Four. The following describes another non-limiting example, and yet another preferred embodiment, of a composition that is encompassed by the present invention. More particularly, the composition includes (or consists of) natural curcumin extract, which is supplemented with additional (and preferably purified) curcumin II, such that the final curcumin II concentration is greater than 15% (w/v). In certain embodiments, the final curcumin II concentration is at least 30% (w/v) curcumin II or, more preferably, at least 50% (w/v) curcumin II. As with the other embodiments described herein, the formulation may be formulated as a capsule, and the capsule may (optionally) comprise additional fillers and agents, such as a vegetable capsule (hydroxypropyl methylcellulose), water, magnesium stearate, and silicon dioxide. In such embodiments, a subject may consume 1-3 capsules per day (and each dose may include, but is not limited to, about 1131 mg of the total composition), to achieve the desired effects described herein.

Example 8—Curcumin Formulation Five. According to yet another preferred embodiment, a composition of the present invention may consist of a combination (mixture) of the curcumin-enriched compositions described in Examples 6 and 7 above.

The many aspects and benefits of the invention are apparent from the detailed description, and thus, it is intended for the following claims to cover all such aspects and benefits of the invention which fall within the scope and spirit of the invention. In addition, because numerous modifications and variations will be obvious and readily occur to those skilled in the art, the claims should not be construed to limit the invention to the exact construction and operation illustrated and described herein. Accordingly, all suitable modifications and equivalents should be understood to fall within the scope of the invention as claimed herein.

What is claimed is:

1. A composition that comprises:
    (a) 30-40% curcumin I;
    (b) 9-11% curcumin II; and
    (c) 45%-55% curcumin III, wherein the composition is formulated as a capsule, pill, tablet, granule, solution or a suspension in an aqueous or non-aqueous liquid, oil-in-water or water-in-oil emulsion, elixir, syrup, paste, or dry powder.

2. The composition of claim 1, which comprises about 35% curcumin I, about 10% curcumin II, and about 50% curcumin III.

3. The composition of claim 1, wherein the composition is formulated as the capsule, which further comprises hydroxypropyl methylcellulose, water, microcrystalline cellulose, magnesium stearate, and silicon dioxide.

4. A composition that comprises:
    (a) 45-55% curcumin I;
    (b) 10-20% curcumin II; and
    (c) 20%-40% curcumin III, wherein the composition is formulated as a capsule, pill, tablet, granule, solution or a suspension in an aqueous or non-aqueous liquid, oil-in-water or water-in-oil emulsion, elixir, syrup, paste, or dry powder.

5. The composition of claim 4, which comprises about 50% curcumin I, about 15% curcumin II, and about 30% curcumin III.

6. The composition of claim 4, wherein the composition is formulated as the capsule, which further comprises hydroxypropyl methylcellulose, water, microcrystalline cellulose, magnesium stearate, and silicon dioxide.

7. A composition that comprises a curcumin extract, which is supplemented with additional (a) curcumin II, (b) curcumin III, or (c) both curcumin II and curcumin III, such that the composition comprises:
    (i) at least 50% curcumin II; or
    (ii) at least 50% curcumin III,
    wherein the composition is formulated as a capsule, pill, tablet, granule, solution or a suspension in an aqueous or non-aqueous liquid, oil-in-water or water-in-oil emulsion, elixir, syrup, paste, or dry powder.

* * * * *

(12) POST-GRANT REVIEW CERTIFICATE (251st)

United States Patent
Cavaleri

(10) Number: US 10,945,970 J1
(45) Certificate Issued: Apr. 5, 2023

(54) CURCUMIN-BASED COMPOSITIONS AND METHODS OF USE THEREOF

(71) Applicant: Franco Cavaleri

(72) Inventor: Franco Cavaleri

Trial Number:

PGR2022-00015 filed Dec. 16, 2021

Post-Grant Review Certificate for:

Patent No.: 10,945,970
Issued: Mar. 16, 2021
Appl. No.: 16/111,502
Filed: Aug. 24, 2018

The results of PGR2022-00015 are reflected in this post-grant review certificate under 35 U.S.C. 328(b).

POST-GRANT REVIEW CERTIFICATE
U.S. Patent 10,945,970 J1
Trial No. PGR2022-00015
Certificate Issued Apr. 5, 2023

AS A RESULT OF THE POST-GRANT REVIEW PROCEEDING, IT HAS BEEN DETERMINED THAT:

Claims 1-7 are cancelled.

\* \* \* \* \*